United States Patent
Wang et al.

(10) Patent No.: US 11,861,897 B2
(45) Date of Patent: Jan. 2, 2024

(54) PORTABLE APPARATUS FOR DETECTING EARLY CROP DISEASES BASED ON SPATIAL FREQUENCY DOMAIN IMAGING AND DETECTION METHOD USING SAME

(71) Applicant: Jiangsu University, Jiangsu (CN)

(72) Inventors: Aichen Wang, Jiangsu (CN); Huadong Cao, Jiangsu (CN); Binjie Gao, Jiangsu (CN); Lin Li, Jiangsu (CN); Xinhua Wei, Jiangsu (CN); Kun Tao, Jiangsu (CN)

(73) Assignee: Jiangsu University, Jiangsu (CN)

( * ) Notice: Subject to any disclaimer, the term of this patent is extended or adjusted under 35 U.S.C. 154(b) by 0 days.

(21) Appl. No.: 18/012,230

(22) PCT Filed: Jan. 14, 2022

(86) PCT No.: PCT/CN2022/071967
§ 371 (c)(1),
(2) Date: Dec. 22, 2022

(87) PCT Pub. No.: WO2023/108852
PCT Pub. Date: Jun. 22, 2023

(65) Prior Publication Data
US 2023/0326203 A1    Oct. 12, 2023

(30) Foreign Application Priority Data

Dec. 15, 2021 (CN) .......................... 202111532071.2

(51) Int. Cl.
*G06V 20/10* (2022.01)
*G06V 10/774* (2022.01)
(Continued)

(52) U.S. Cl.
CPC .......... *G06V 20/188* (2022.01); *G01N 21/84* (2013.01); *G03B 17/02* (2013.01); *G06T 5/001* (2013.01);
(Continued)

(58) Field of Classification Search
CPC .... G06V 20/188; G06V 10/774; G06V 10/46; H04N 23/51; H04N 23/54; H04N 23/56;
(Continued)

(56) References Cited

U.S. PATENT DOCUMENTS 5,155,558 A * 10/1992 Tannenbaum ......... G01N 21/47
356/124.5
2008/0101657 A1 * 5/2008 Durkin ............... G01N 21/4795
382/110
(Continued)

FOREIGN PATENT DOCUMENTS

| CN | 105466889 | 4/2016 |
| CN | 105510253 | 4/2016 |

(Continued)

OTHER PUBLICATIONS

Dong Hu ; et al., "Spatial-frequency domain imaging coupled with frequency optimization for estimating optical properties of two-layered food and agricultural products," Journal of Food Engineering, vol. 277, 109909, Jul. 2020, pp. 1-13.
(Continued)

*Primary Examiner* — Matthew David Kim
(74) *Attorney, Agent, or Firm* — JCIPRNET

(57) ABSTRACT

The present disclosure provides a portable apparatus for detecting early crop diseases based on spatial frequency domain imaging. The apparatus includes an end cover, a spatial frequency domain imaging apparatus, a dark box body, a telescopic section, and an opening-and-closing apparatus connected in sequence. The detection method includes:
(Continued)

putting a crop sample to be detected into the dark box body from a bottom; projecting structured light of sine grey scale patterns with different spatial frequencies to the crop sample; after the sine gray scale pattern is switched each time, acquiring, by a camera, a diffuse reflection image of a surface of the crop sample once; after capturing all diffuse reflection images, performing uniformity correction on the images, demodulating the images, and extracting an alternating current component; and inputting an alternating current component image to a trained disease detection model, and determining whether the crop sample has a disease.

20 Claims, 7 Drawing Sheets

(51) Int. Cl.
| | | |
|---|---|---|
| G06V 10/46 | (2022.01) | |
| H04N 23/51 | (2023.01) | |
| H04N 23/54 | (2023.01) | |
| H04N 23/56 | (2023.01) | |
| G01N 21/84 | (2006.01) | |
| G03B 17/02 | (2021.01) | |
| G06T 5/00 | (2006.01) | |
| G06T 7/00 | (2017.01) | |
| H01S 5/024 | (2006.01) | |

(52) U.S. Cl.
CPC ............ *G06T 7/0002* (2013.01); *G06V 10/46* (2022.01); *G06V 10/774* (2022.01); *H01S 5/02415* (2013.01); *H04N 23/51* (2023.01); *H04N 23/54* (2023.01); *H04N 23/56* (2023.01); *G01N 2021/8466* (2013.01); *G01N 2201/0633* (2013.01); *G01N 2201/0636* (2013.01); *G01N 2201/06113* (2013.01); *G06T 2207/20081* (2013.01); *G06T 2207/30188* (2013.01)

(58) Field of Classification Search
CPC ........ G01N 21/84; G03B 17/02; G06T 5/001; G06T 7/0002; H01S 5/02415
USPC .......................................................... 348/158
See application file for complete search history.

(56) References Cited

U.S. PATENT DOCUMENTS

| | | | |
|---|---|---|---|
| 2010/0026966 A1* | 2/2010 | Nakano | G03B 21/16 |
| | | | 362/373 |
| 2017/0105618 A1* | 4/2017 | Schmoll | G02B 21/0056 |
| 2019/0117078 A1* | 4/2019 | Sharma | A61B 1/24 |
| 2019/0324240 A1* | 10/2019 | Shroff | G02B 21/0048 |
| 2020/0134773 A1* | 4/2020 | Pinter | G01N 21/8806 |
| 2020/0342205 A1* | 10/2020 | Park | G01N 21/6458 |
| 2021/0112647 A1* | 4/2021 | Coleman | H05B 47/16 |
| 2022/0208068 A1* | 6/2022 | Choi | H10K 59/353 |
| 2023/0333374 A1* | 10/2023 | Collings | G02B 27/0172 |

FOREIGN PATENT DOCUMENTS

| | | |
|---|---|---|
| CN | 106950196 | 7/2017 |
| CN | 107000118 | 8/2017 |
| CN | 110044898 | 7/2019 |
| CN | 112229847 | 1/2021 |
| CN | 113256575 | 8/2021 |

OTHER PUBLICATIONS

Zhong Wang ; et al., "Application status and perspective of spatial-frequency domain imaging in quality evaluation of agricultural products," Transactions of the Chinese Society of Agricultural Engineering, vol. 37 No. 15, Aug. 2021, pp. 275-288.

"International Search Report (Form PCT/ISA/210) of PCT/CN2022/071967," dated Sep. 21, 2022, pp. 1-5.

"Written Opinion of the International Searching Authority (Form PCT/ISA/237) of PCT/CN2022/071967," dated Sep. 21, 2022, pp. 1-4.

* cited by examiner

PORTABLE APPARATUS FOR DETECTING EARLY CROP DISEASES BASED ON SPATIAL FREQUENCY DOMAIN IMAGING AND DETECTION METHOD USING SAME

CROSS-REFERENCE TO RELATED APPLICATION

This application is a 371 of international application of PCT application serial no. PCT/CN2022/071967, filed on Jan. 14, 2022, which claims the priority benefit of China application no. 202111532071.2, filed on Dec. 15, 2021. The entirety of each of the above mentioned patent applications is hereby incorporated by reference herein and made a part of this specification.

TECHNICAL FIELD

The present disclosure belongs to the technical field of nondestructive detection, and specifically, relates to a portable apparatus for detecting early crop diseases based on spatial frequency domain imaging and a detection method using the same.

BACKGROUND

Crop diseases usually lead to the decline of crop quality and yield, and are an important factor threatening national food security. The early stage of crop disease infection is a weak period in the process of pathogen infection. In order to alleviate the impact of crop diseases, it is necessary to implement early detection and early prevention. Therefore, it is of great significance to implement early detection of crop diseases. A conventional manner of disease detection is mainly an expert identification method, which relies on the experience of agricultural experts to diagnose, but this method is strongly subjective, inaccurate, and inefficient. In addition, an isolation and culture detection method and a serum detection method need to destroy a plant structure, and suffer from limitations.

In recent years, a spatial frequency domain imaging (SFDI) technology has gradually attracted attention from related researchers due to its features such as a high analysis speed and no need to destroy samples. In the spatial frequency domain imaging (SFDI) technology, spatially modulated sine structured light is used to illuminate a sample to be detected, and the optical absorption and scattering properties of the sample tissue are analyzed by capturing diffuse reflection images of the sample. However, due to the shortcomings, such as an excessively large volume and a difficulty to move, of the apparatus for implementing this technology, a role of the technology in real-time disease detection is greatly limited. Therefore, it is significant to develop a portable disease detection apparatus that can not only image in a wide field of view, but also be convenient for use in the field.

SUMMARY

In view of the shortcomings of the prior art, the present disclosure provides a portable apparatus for detecting early crop diseases based on spatial frequency domain imaging and a detection method using the same. Rapid and nondestructive detection of early diseases of crops in the field is achieved by projecting structured light to a crop to be detected and collecting its reflected images.

In the present disclosure, the foregoing technical objective is achieved by using the following technical means.

A portable apparatus for detecting early crop diseases based on spatial frequency domain imaging is provided, including an end cover, a dark box body, a spatial frequency domain imaging apparatus, a telescopic section, and an opening-and-closing apparatus that are connected from top to bottom;

the spatial frequency domain imaging apparatus includes a square box housing, light source modules, collimating lenses, dichroic mirrors, an achromatic lens, a first linear polarizer, a second linear polarizer, a camera, a reflector, and a digital micromirror apparatus; the collimating lenses, the dichroic mirrors, the achromatic lens, the reflector, and the digital micromirror apparatus are all mounted inside the square box housing; the light source modules are separately mounted on two adjacent side surfaces of the square box housing, the collimating lens is opposite to the light source module, and a center of the dichroic mirror is located on an axis of the collimating lens; a center of the digital micromirror apparatus is separately located on a straight line running through the center of the dichroic mirror and on an axis of the achromatic lens; a center of the reflector is separately located on the axis of the achromatic lens and on an axis of the first linear polarizer; the camera is vertically mounted at a bottom of the square box housing, and a lens passes through the square box housing and shoots downward; and the second linear polarizer is mounted in front of the lens of the camera; and the opening-and-closing apparatus includes sector skeletons, middle sections, and opening-and-closing skeletons, the middle section is internally connected to a light-shielding cloth, the middle section is externally connected to the sector skeleton, and each of two ends of the middle section is provided with one opening-and-closing skeleton, the light-shielding cloth is provided with an opening at the opening-and-closing skeleton, an outer circumference of the sector skeleton is provided with a guide rail for movement of the opening-and-closing skeleton; and the middle section is made of an elastic material.

In the foregoing technical solution, the light source module includes a laser diode, a thermoelectric cooler (TEC) refrigeration sheet, and a radiator, where the laser diode is pasted on a heat absorption surface of the TEC refrigeration sheet, and a heat dissipation surface of the TEC refrigeration sheet is mounted on the radiator.

In the foregoing technical solution, an annular heat insulation ring is sleeved outside the laser diode and the TEC refrigeration sheet.

In the foregoing technical solution, a polarization angle of the first linear polarizer and the second linear polarizer is 90 degrees.

In the foregoing technical solution, the dark box body includes a dark box shell, an annular boss, and an observation port cover, where the annular boss is located on an upper end inside the dark box shell, the observation port cover is located on a lower part of the dark box shell, and is rotatably connected to the dark box shell; and the dark box shell is equipped with a cooling fan mounted close to the light source module.

In the foregoing technical solution, several groups of the telescopic section and the opening-and-closing apparatus are sequentially mounted at a bottom of the detection apparatus.

A detection method using the portable apparatus for detecting early crop diseases based on spatial frequency domain imaging is provided, specifically including the following steps:

rotating the opening-and-closing skeleton, opening the light-shielding cloth, and putting a crop to be detected into the dark box body from a bottom;

adjusting a shooting distance of the crop sample to a suitable distance through an observation port;

closing the opening-and-closing apparatus, selecting a suitable projection optical wavelength, controlling the spatial frequency domain imaging apparatus to project structured light of sine grey scale patterns with different spatial frequencies to the crop sample to be detected; after the sine gray scale pattern is switched each time, acquiring, by the camera, a diffuse reflection image of a surface of the crop sample once;

after capturing all diffuse reflection images, performing uniformity correction on the images, demodulating the images, and extracting an alternating current component; and inputting the alternating current component image to a trained disease detection model, and determining whether the crop to be detected has a disease and a type of the disease.

Further, each spatial frequency adopts three phases: 0, 2 π/3, and 4 π/3.

Furthermore, a specific process of the image modulation includes:

demodulating the diffuse reflection image by using a formula $$M_{AC}(x, f_x) = \frac{\sqrt{2}}{3}\left[(I_1 - I_2)^2 + (I_2 - I_3)^2 + (I_3 - I_1)^2\right],$$

to obtain a diffuse reflection amplitude envelope curve of the crop to be detected; and then calculating the alternating current component of the image by using the formula $I_{AC}(x, f_x) = MA_{AC}(x, f_x) \cdot \cos(2\pi f_x + \alpha)$;

where $I_1$, $I_2$, and $I_3$ are respectively reflection intensities of pixels of the diffuse reflection image of the sample to be detected in three phases, $f_x$ is a spatial frequency of a light source, and $\alpha$ is a spatial phase of the light source.

Furthermore, the trained disease detection model is obtained by the following steps:

extracting features of the alternating current component of the diffuse reflection image, clustering the extracted features, constructing a Bag of words, classifying all the features of the alternating current component image into different categories, then collecting statistics on a frequency of each category of features, using the Bag of words of each picture as a feature vector, using a category of the picture as a label, and performing training to obtain the disease detection model.

The beneficial effects of the present disclosure are as follows. The spatial frequency domain imaging apparatus of the present disclosure includes a square box housing, light source modules, collimating lenses, dichroic mirrors, an achromatic lens, a first linear polarizer, a second linear polarizer, a camera, a reflector, and a digital micromirror apparatus; the light source modules are separately mounted on two adjacent side surfaces of the square box housing, the collimating lens is opposite to the light source module, and a center of the dichroic mirror is located on an axis of the collimating lens; a center of the digital micromirror apparatus is separately located on a straight line running through centers of two dichroic mirrors and on an axis of the achromatic lens; a center of the reflector is separately located on the axis of the achromatic lens and on an axis of the first linear polarizer; the camera is vertically mounted at a bottom of the square box housing, and a lens passes through the square box housing and shoots downward; and the second linear polarizer is mounted in front of the lens of the camera. During operation, the light source module emits light, the light passes through the collimating lens and the dichroic mirror onto the digital micromirror apparatus; the digital micromirror apparatus reflects structured light with a sine stripe pattern; the structured light passes through the achromatic lens; after being reflected by the reflector, the structured light passes downward through the first linear polarizer onto the crop to be detected; the reflected light on the surface of the crop to be detected passes through the second linear polarizer, and is received by the camera; the camera transmits acquired image data to a computer for subsequent processing. The opening-and-closing apparatus includes sector skeletons, middle sections made of elastic materials, and opening-and-closing skeletons; the middle section is internally connected to a light-shielding cloth, the middle section is externally connected to the sector skeleton, the light-shielding cloth is laid between sector skeletons, each of two ends of the middle section is provided with an opening-and-closing skeleton, the light-shielding cloth is provided with an opening at the opening-and-closing skeleton, and an outer circumference of the sector skeleton is provided with a guide rail for movement of the opening-and-closing skeleton. The portable spatial frequency domain imaging apparatus of the present disclosure can implement real-time detection of early crop diseases in the field by combining darkroom conditions formed by the dark box body and the opening-and-closing apparatus, improve portability of the spatial frequency domain imaging apparatus, and also has advantages of wide field imaging and low costs.

In the figures: 1. End cover; 2. Dark box body; 3. Spatial frequency domain imaging apparatus; 4. Telescopic section; 5. Opening-and-closing apparatus; 201. Cylindrical dark box shell; 202. Threaded hole; 203. Annular boss; 204:

Cooling fan; 205. Observation port cover; 301. Light source module; 302. Collimating lens; 303. Dichroic mirror; 304. Digital micromirror apparatus control board; 305. Achromatic lens; 306. First linear polarizer; 307. Second linear polarizer; 308. Camera; 309. Reflector; 310. Light source module controller; 311. Fixed ear plate; 312. Digital micromirror apparatus; 313. Laser diode; 314. TEC refrigeration sheet; 315. Heat insulation ring; 316. Radiator; 317. Square box housing; 501. Sector skeleton; 502. Middle section; 503. Support bracket; 504. Light-shielding cloth; 505. Opening-and-closing skeleton.

DETAILED DESCRIPTION OF THE EMBODIMENTS

The following further describes the present disclosure with reference to the accompanying drawings and specific embodiments, but the protection scope of the present disclosure is not limited thereto.

The following clearly and completely describes the technical solutions of the present disclosure with reference to the accompanying drawings. Apparently, the described embodiments are merely some rather than all of the embodiments of the present disclosure. Based on the embodiments of the present disclosure, all other embodiments obtained by those of ordinary skill in the art without creative effort fall within the protection scope of the present disclosure.

Figure 1:
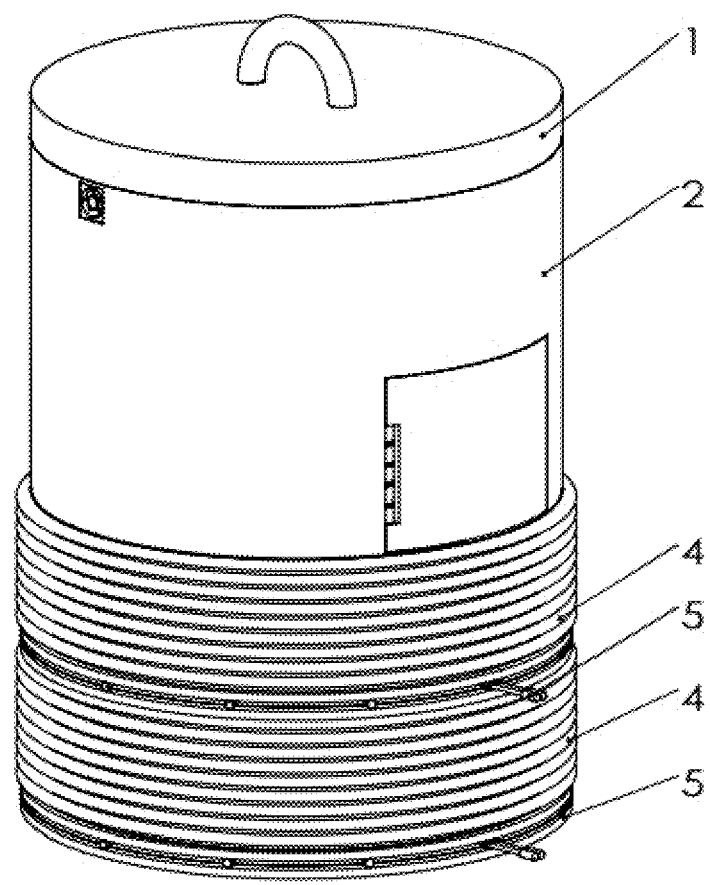
FIG. 1 is an axonometrical drawing of the portable apparatus for detecting early crop diseases according to the present disclosure.
Figure 2:
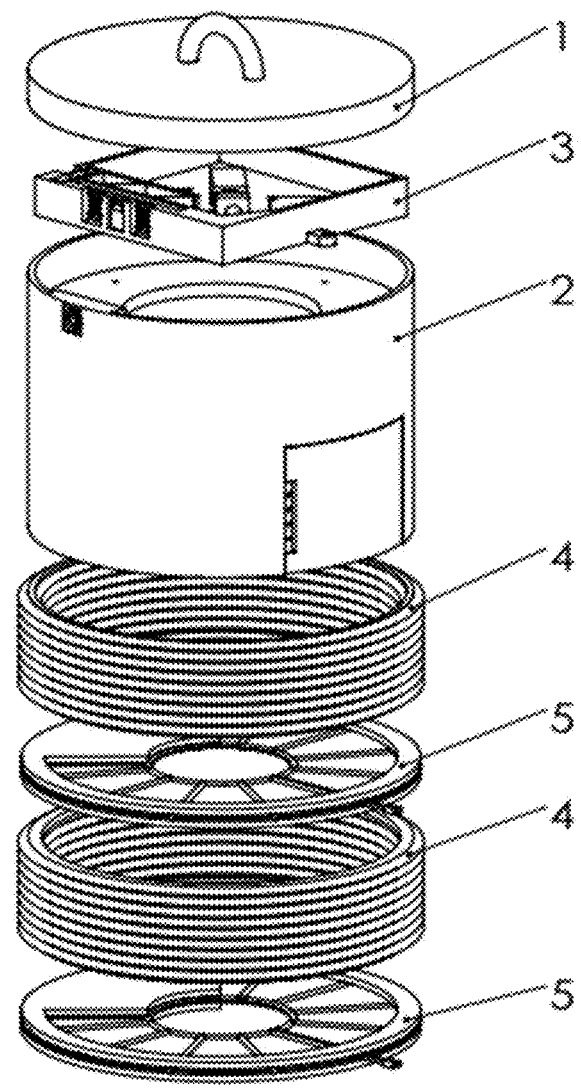
FIG. 2 is an exploded view of the portable apparatus for detecting early crop diseases according to the present disclosure.

As shown in FIG. 1 and FIG. 2, a portable apparatus for detecting early crop diseases based on spatial frequency domain imaging of the present disclosure includes the end cover 1, the dark box body 2, the spatial frequency domain imaging apparatus 3, two telescopic sections 4, and two opening-and-closing apparatuses 5. The spatial frequency domain imaging apparatus 3 is mounted on the annular boss 203 inside the dark box body 2. The end cover 1 is mounted on top of the dark box body 2. The telescopic section 4 is mounted at the bottom of the dark box body 2. The opening-and-closing apparatus 5 is mounted at the bottom of the telescopic section 4. In this embodiment, one telescopic section 4 and one opening-and-closing apparatus 5 are continuously mounted at the bottom of the opening-and-closing apparatus 5 in the same order, or the telescopic section 4 and the opening-and-closing apparatus 5 are continuously added based on an actual requirement. The telescopic section 4 is used for crops with different heights.

Figure 3:
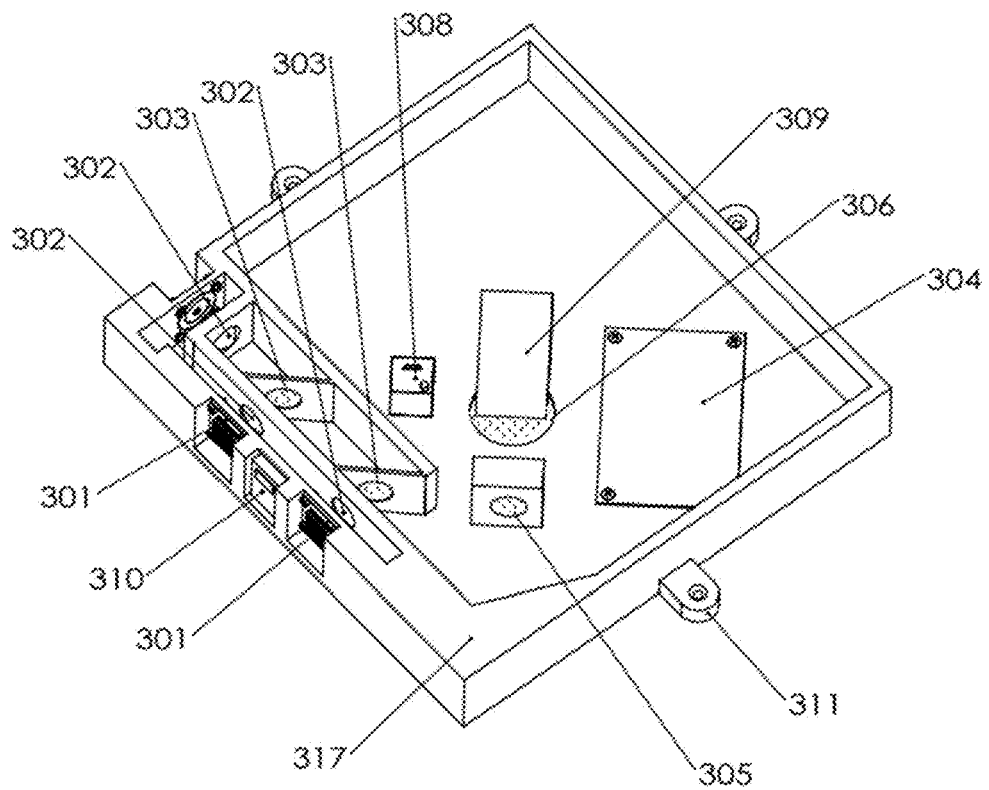
FIG. 3 is a side view of the spatial frequency domain imaging apparatus according to the present disclosure.
Figure 4:
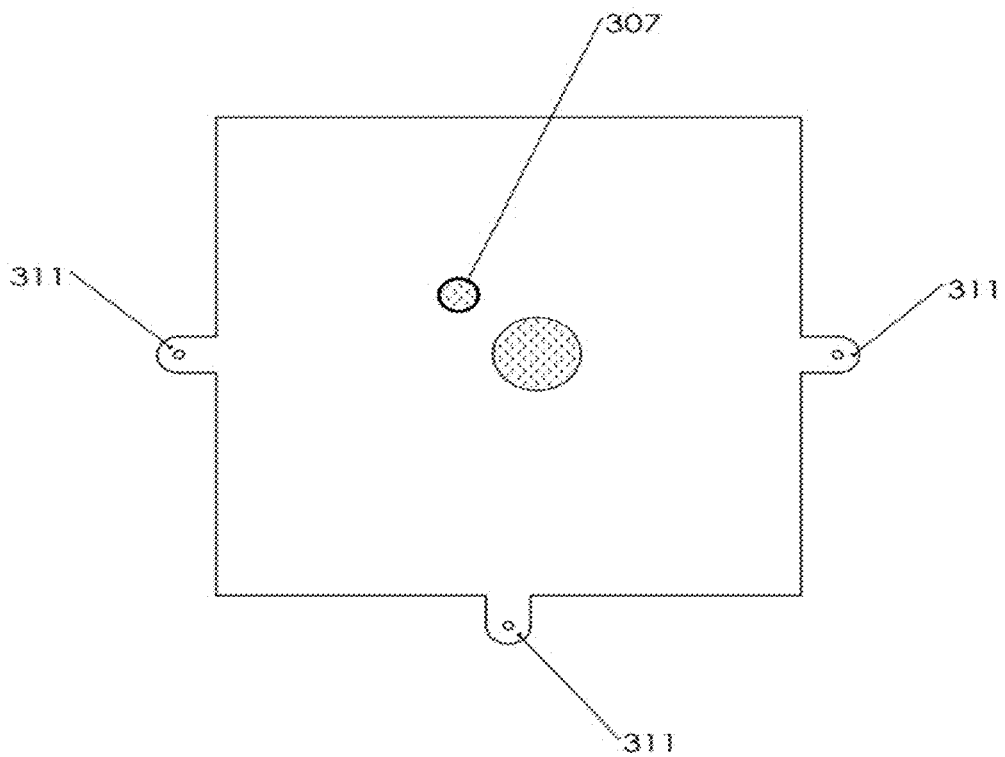
FIG. 4 is a bottom view of the spatial frequency domain imaging apparatus according to the present disclosure.
Figure 5:
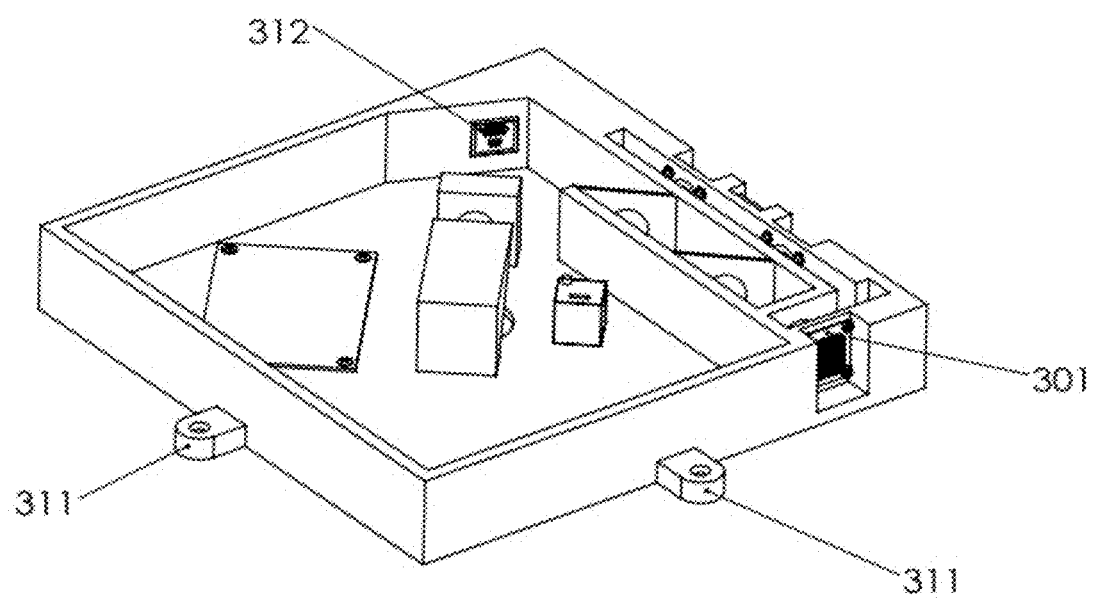
FIG. 5 is another side view of the spatial frequency domain imaging apparatus according to the present disclosure.

As shown in FIG. 3, FIG. 4, and FIG. 5, the spatial frequency domain imaging apparatus 3 includes the square box housing 317, three light source modules 301, three collimating lenses 302, two dichroic mirrors 303, the digital micromirror apparatus control board 304, the achromatic lens 305, the first linear polarizer 306, the second linear polarizer 307, the camera 308, the reflector 309, the light source module controller 310, fixed ear plates 311, and the digital micromirror apparatus 312. The three light source modules 301 are connected to the light source module controller 310, and both the digital micromirror apparatus 312 and the camera 308 are connected to a computer. Two light source modules 301 are mounted on one side of the square box housing 317, and the collimating lenses 302, the dichroic mirrors 303, the digital micromirror apparatus 312, the achromatic lens 305, and the reflector 309 are all mounted on a support bracket inside the square box housing 317. Two collimating lenses 302 are respectively opposite to the two light source modules 301. Centers of the two dichroic mirrors 303 are located on axes of the two collimating lenses 302. The third light source module 301 is mounted on another side of the square box housing 317 which is adjacent to the two light source modules 301 (to be specific, light of the third light source module 301 is perpendicular to light of the two light source modules 301). The third collimating lens 302 is mounted on an inner side of the third light source module 301. The third collimating lens 302 is opposite to the third light source module 301, and an axis of the third collimating lens 302 runs through centers of the two dichroic mirrors 303. A center of the digital micromirror apparatus 312 is located on a straight line running through the centers of the two dichroic mirrors 303. The center of the digital micromirror apparatus 312 is further located on an axis of the achromatic lens 305. A center of the reflector 309 is located on the axis of the achromatic lens 305, and the center of the reflector 309 is further located on an axis of the first linear polarizer 306. The first linear polarizer 306 is mounted in a hole at the bottom of the square box housing 317. The light source module controller 310 is mounted on the square box housing 317. The digital micromirror apparatus control board 304 is fixed to the bottom of the square box housing 317 through a threaded connection. The second linear polarizer 307 is mounted in front of a lens of the camera 308. The camera 308 is vertically mounted at the bottom of the square box housing 317, and a lens extends out of a reserved hole of the square box housing 317 and shoots downward.

Figure 6:
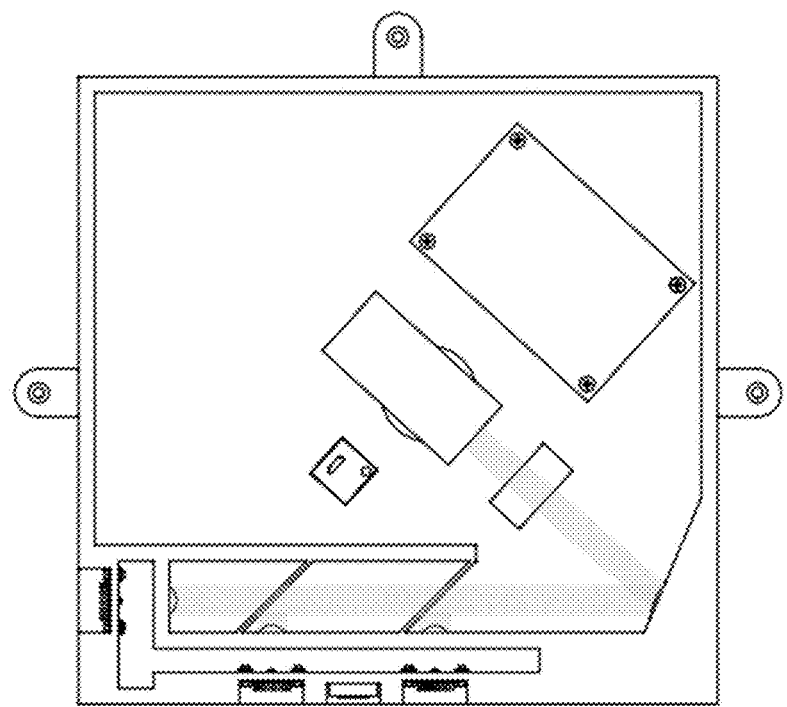
FIG. 6 is a diagram of an internal light path of the spatial frequency domain imaging apparatus according to the present disclosure.

As shown in FIG. 6, the light source module 301 is controlled by the light source module controller 310 to emit light, the light passes through the collimating lens 302 and the dichroic mirror 303 onto the digital micromirror apparatus 312; the digital micromirror apparatus 312 is controlled by the computer to reflect structured light with a sine stripe pattern; the structured light passes through the achromatic lens 305; after being reflected by the reflector 309, the structured light passes downward through the first linear polarizer 306 onto a crop to be detected; the reflected light on a surface of the crop to be detected passes through the second linear polarizer 307, and is received by the camera 308; and the camera 308 transmits acquired image data to the computer for subsequent processing.

A polarization angle of the first linear polarizer 306 and the second linear polarizer 307 is 90 degrees, to weaken specular reflection on the surface of the sample to be detected, and improve an image demodulation effect. Mounting positions of the three light source modules 301 are reserved on the square box housing 317 and the light source modules 301 with three different wavelengths can be mounted. Under control of the light source module controller 310, an image of a sample tissue illuminated by structured light with different wavelengths or a mixture of several wavelengths may be collected to determine a wavelength with optimal performance for the sample. Image switching of the digital micromirror apparatus 312 is controlled by the computer to be in a same period as acquisition of the camera 308.

Figure 7:
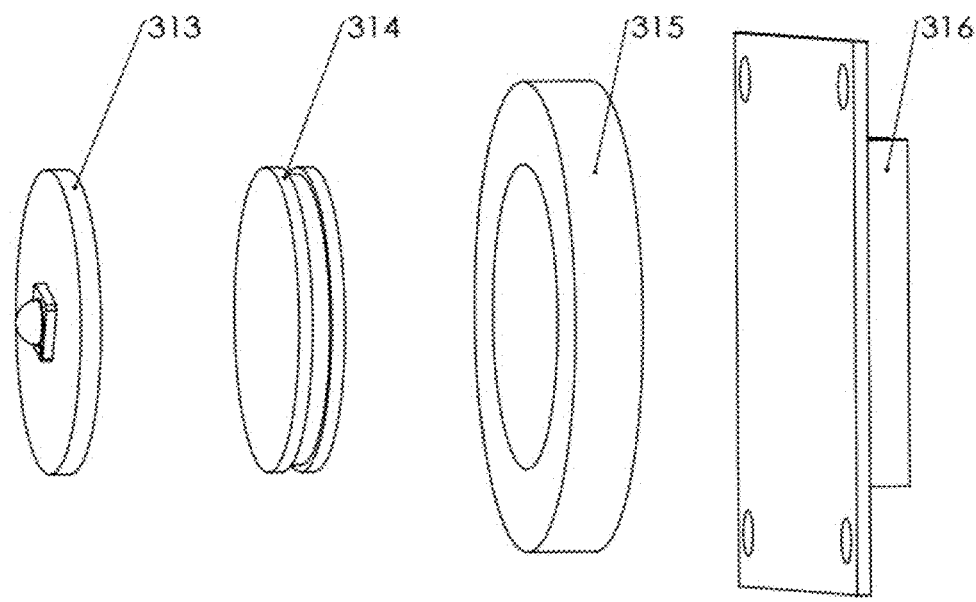
FIG. 7 is a schematic diagram of a composition of the light source module according to the present disclosure.

As shown in FIG. 7, the light source module 301 includes the laser diode 313, the TEC refrigeration sheet 314, the heat insulation ring 315, and the radiator 316. The laser diode 313 is pasted on a heat absorption surface of the TEC refrigeration sheet 314 by using a heat conductive adhesive. An annular heat insulation ring 315 is sleeved outside the two for alleviating impact of heat dissipated by the laser diode 313 on remaining devices. The heat insulation ring 315 and a heat dissipation surface of the TEC refrigeration sheet 314 are mounted on the radiator 316. Four corners of the radiator 316 are provided with holes, for mounting the light source module 301 on the square box housing 317. The TEC performs refrigeration by using a Peltier effect of a semiconductor. When a direct current power supply passes through a couple consisting of two semiconductor materials, a phenomenon that one end absorbs heat and the other end dissipates heat occurs. Heat of the TEC refrigeration sheet 314 can be transferred from one side to the other side by using this phenomenon, to reduce a temperature of the laser diode 313, thereby prolonging its service life and ensuring light source stability.

Figure 8:
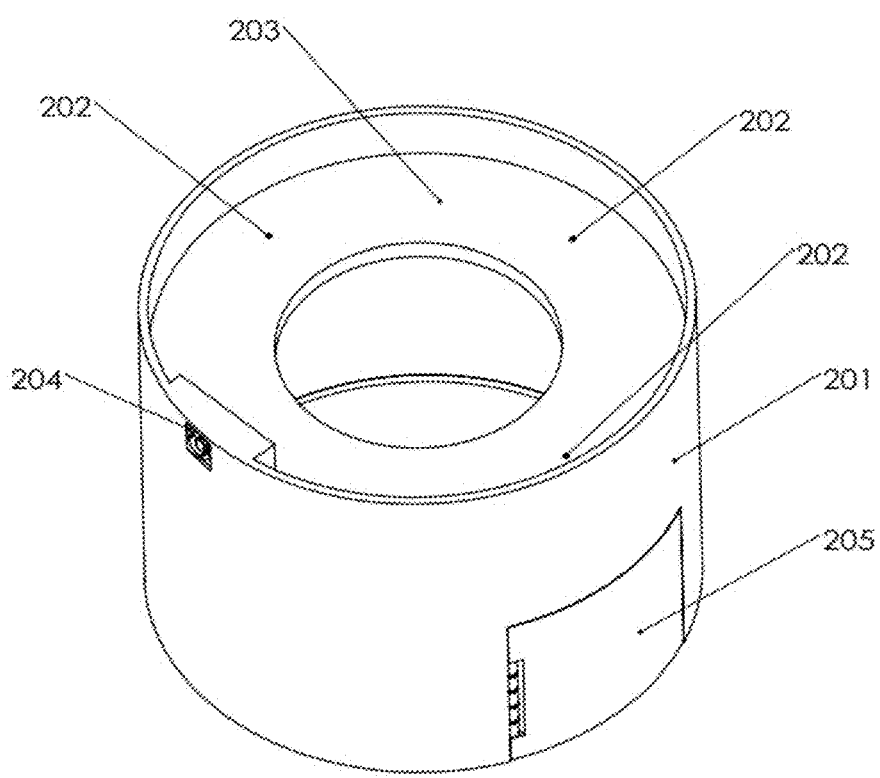
FIG. 8 is a structural diagram of the cylindrical dark box body according to the present disclosure.

As shown in FIG. 8, the dark box body 2 includes the dark box shell 201, threaded holes 202, the annular boss 203, the cooling fan 204, and the observation port cover 205. The end cover 1 is mounted on a top end of the dark box body 2. The annular boss 203 is located on an upper end inside the dark box shell 201. The annular boss 203 is provided with three mounting threaded holes 202 corresponding to the fixed ear plates 311 that are integrated in the spatial frequency imaging domain apparatus 3, to ensure that the spatial frequency domain imaging apparatus 3 is mounted at a fixed position. The dark box shell 201 is provided with a square through hole close to the light source module 301, for mounting the cooling fan 204 to cool the light source module.

An observation port is provided on a lower part of the dark box body 2 for manual observation of a height for capturing images of the crop. The observation port cover 205 is connected to the dark box shell 201 through a rotating shaft. When a suitable height for capturing images is determined, the observation port can be closed to form a darkroom environment. The bottom of the cylindrical dark box body 2 is connected to the telescopic section 4. The telescopic section is made of a flexible material, and the height for capturing images can be changed within a particular range.

Figure 9:
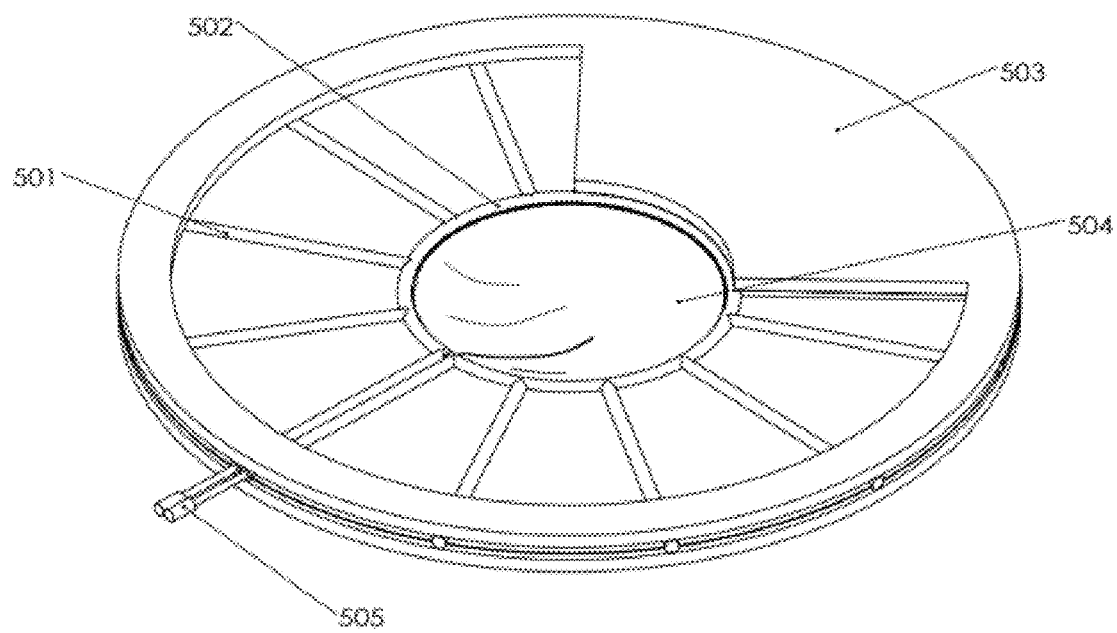
FIG. 9 is a schematic structural diagram of the opening-and-closing apparatus according to the present disclosure.

As shown in FIG. 9, the opening-and-closing apparatus 5 includes sector skeletons 501, middle sections 502, support brackets 503, the light-shielding cloth 504, and opening-and-closing skeletons 505. The middle section 502 is annular, and is located at a center of the opening-and-closing apparatus 5. The middle section 502 is made of an elastic rubber material. The middle section 502 is internally connected to the light-shielding cloth 504. The middle section 502 is externally connected to the sector skeleton 501. The light-shielding cloth 504 is laid between sector skeletons 501. A part of the sector skeleton 501 is a sealed sector structure and is used as the support bracket 503. The support bracket 503 is used to connect to another component, and the middle section 502 is embedded into the support bracket 503. Each of two ends of the middle section 502 is provided with one long opening-and-closing skeleton 505, for manually opening and closing an entire sector. The internal light-shielding cloth 504 is provided with an opening at the opening-and-closing skeleton 505. When the two opening-and-closing skeletons 505 are closed, the internal light-shielding cloth 504 can adhere to a stem of the crop tightly, to prevent light from passing through. A guide rail for movement of the opening-and-closing skeleton 505 is provided inside an outer circumference of the sector skeleton 501.

A manner of connection between the opening-and-closing apparatus 5, the telescopic section 4, and the cylindrical dark box body 2, and a manner of wiring between the light source module 301, the digital micromirror apparatus 312, the camera 308, and the cooling fan 204 and the outside are not drawn in the drawings of the present disclosure.

Figure 10:
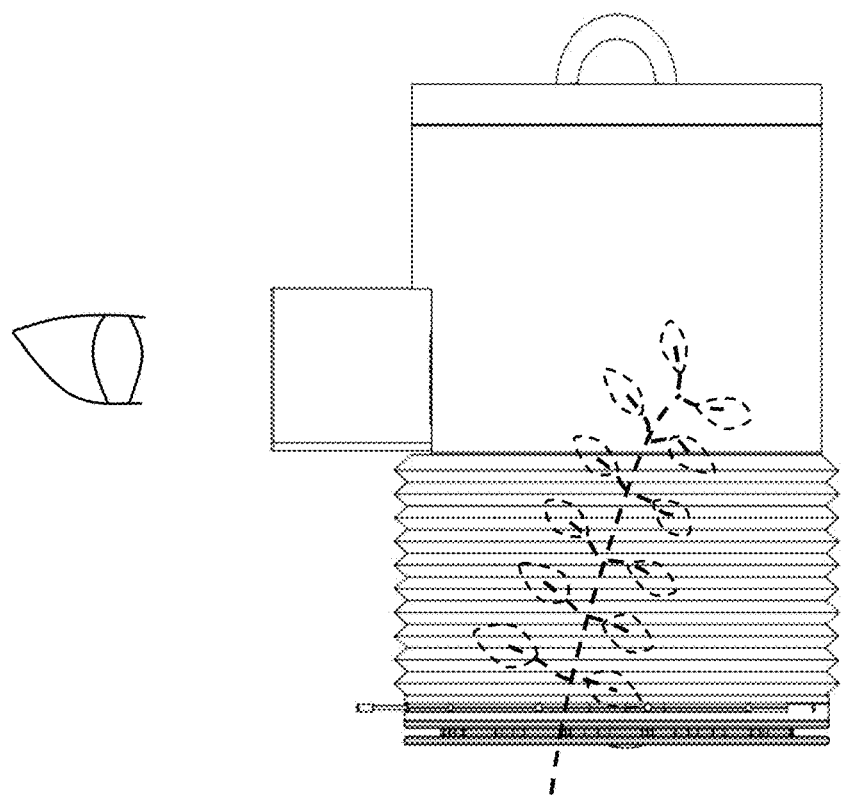
FIG. 10 is a schematic diagram of height observation of the crop according to the present disclosure.
Figure 11:
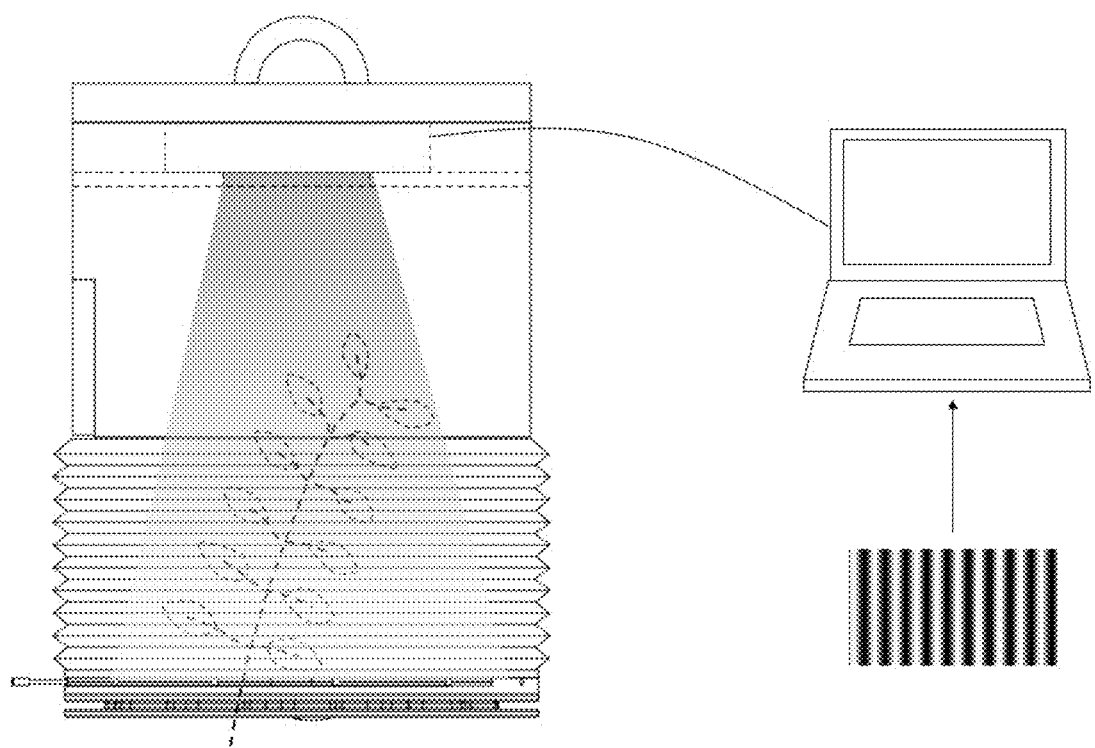
FIG. 11 is a schematic diagram of the detection manner according to the present disclosure.

A detection method for early crop diseases based on spatial frequency domain imaging includes the following steps:

the opening-and-closing skeleton 505 is rotated to open the light-shielding cloth 504, and a crop to be detected is input into the dark box body 2 from the bottom; as shown in FIG. 10, the observation port cover 205 is opened to observe a shooting distance of the crop sample to be detected, and the shooting distance of the crop sample is adjusted to a suitable distance before the observation port cover 205 is closed;

as shown in FIG. 11, all the opening-and-closing apparatuses 5 are closed, a suitable projection optical wavelength is selected by using the light source module controller 310, then the spatial frequency domain imaging apparatus 3 is controlled by the computer to project structured light of sine grey scale patterns with different spatial frequencies (each spatial frequency adopts three phases: 0, 2 π/3, and 4 π/3) to the crop sample to be detected; after the sine gray pattern is switched each time, the camera 308 is controlled to acquire a diffuse reflection image of a surface of the crop sample once; after all the diffuse reflection images are captured, all the opening-and-closing apparatuses 5 are opened and the crop sample is replaced with a reference whiteboard whose height is the same as the crop sample, and the foregoing operations are repeated;

uniformity correction is performed on the diffuse reflection image, the image is demodulated, and an alternating current component is extracted; and the alternating current component image is input to a trained disease detection model, and whether the crop to be detected has a disease is determined.

Further, specific steps of the image modulation are as follows.

First, uniformity correction is performed by using the following formula:

$$R' = \frac{I - I_{dark}}{I_{white} - I_{dark}}$$

In the formula, R' is an image diffuse reflection intensity after correction, $I_{dark}$ is a dark field image intensity, and $I_{white}$ is a reference whiteboard image intensity under illumination of planar light.

Next, demodulation is performed by using the following formula, to obtain a diffuse reflection amplitude envelope curve of the sample:

$$M_{AC}(x, f_x) = \frac{\sqrt{2}}{3}\left[(I_1 - I_2)^2 + (I_2 - I_3)^2 + (I_3 - I_1)^2\right]$$

In the formula, $I_1$, $I_2$, and $I_3$ are respectively reflection intensities of pixels of the diffuse reflection image of the sample to be detected in the three phases of each spatial frequency.

Finally, the alternating current component of the image is calculated by using the following formula:

$$I_{AC}(x, f_x) = MA_{AC}(x, f_x) \cdot \cos(2\pi f_x + \alpha)$$

In the formula, $f_x$ is a spatial frequency of a light source, and α is a spatial phase of the light source.

Further, specific steps of obtaining the trained disease detection model are as follows:

(1) features of the alternating current component of the diffuse reflection image are extracted by using a surf algorithm;

(2) the extracted features are clustered by using a Kmeans algorithm;

(3) a Bag of words is constructed, all the features of the alternating current component image are classified into different categories, and then statistics are collected on a frequency of each category of features; and (4) the Bag of words of each picture is used as a feature vector, a category of the picture is used as a label, and training is performed by using an SVM to obtain the disease detection model.

The embodiments are preferred embodiments of the present disclosure, but the present disclosure is not limited to the foregoing implementations. Without departing from the essential content of the present disclosure, any obvious improvement, replacement, or modification that can be made by a person skilled in the art belongs to the protection scope of the present disclosure.

What is claimed is:

1. A portable apparatus for detecting early crop diseases based on spatial frequency domain imaging, comprising an end cover, a dark box body, a spatial frequency domain imaging apparatus, a telescopic section, and an opening-and-closing apparatus that are connected from top to bottom;
   the spatial frequency domain imaging apparatus comprises a square box housing, light source modules, collimating lenses, dichroic mirrors, an achromatic lens, a first linear polarizer, a second linear polarizer, a camera, a reflector, and a digital micromirror apparatus; the collimating lenses, the dichroic mirrors, the achromatic lens, the reflector, and the digital micromirror apparatus are all mounted inside the square box housing; the light source modules are separately mounted on two adjacent side surfaces of the square box housing, the collimating lens is opposite to the light source module, and a center of the dichroic mirror is located on an axis of the collimating lens; a center of the digital micromirror apparatus is separately located on a straight line running through the center of the dichroic mirror and on an axis of the achromatic lens; a center of the reflector is separately located on the axis of the achromatic lens and on an axis of the first linear polarizer; the camera is vertically mounted at a bottom of the square box housing, and a lens passes through the square box housing and shoots downward; and the second linear polarizer is mounted in front of the lens of the camera; and
   the opening-and-closing apparatus comprises sector skeletons, middle sections, and opening-and-closing skeletons, the middle section is internally connected to a light-shielding cloth, the middle section is externally connected to the sector skeleton, and each of two ends of the middle section is provided with one opening-and-closing skeleton, the light-shielding cloth is provided with an opening at the opening-and-closing skeleton, an outer circumference of the sector skeleton is provided with a guide rail for movement of the opening-and-closing skeleton; and the middle section is made of an elastic material.

2. The portable apparatus for detecting early crop diseases according to claim 1, wherein the light source module comprises a laser diode, a thermoelectric cooler (TEC) refrigeration sheet, and a radiator, wherein the laser diode is pasted on a heat absorption surface of the TEC refrigeration sheet, and a heat dissipation surface of the TEC refrigeration sheet is mounted on the radiator.

3. The portable apparatus for detecting early crop diseases according to claim 2, wherein an annular heat insulation ring is sleeved outside the laser diode and the TEC refrigeration sheet.

4. The portable apparatus for detecting early crop diseases according to claim 1, wherein a polarization angle of the first linear polarizer and the second linear polarizer is 90 degrees.

5. The portable apparatus for detecting early crop diseases according to claim 1, wherein the dark box body comprises a dark box shell, an annular boss, and an observation port cover, wherein the annular boss is located on an upper end inside the dark box shell, the observation port cover is located on a lower part of the dark box shell, and is rotatably connected to the dark box shell; and the dark box shell is equipped with a cooling fan mounted close to the light source module.

6. The portable apparatus for detecting early crop diseases according to claim 1, wherein several groups of the telescopic section and the opening-and-closing apparatus are sequentially mounted at a bottom of the detection apparatus.

7. A detection method using the portable apparatus for detecting early crop diseases according to claim 1, comprising the following steps:
   rotating the opening-and-closing skeleton, opening the light-shielding cloth, and putting a crop sample to be detected into the dark box body from a bottom;
   adjusting a shooting distance of the crop sample to a suitable distance through an observation port;
   closing the opening-and-closing apparatus, selecting a suitable projection optical wavelength, controlling the spatial frequency domain imaging apparatus to project structured light of sine grey scale patterns with different spatial frequencies to the crop sample to be detected; after the sine gray scale pattern is switched each time, acquiring, by the camera, a diffuse reflection image of a surface of the crop sample once; and opening all the opening-and-closing apparatuses, replacing the crop sample with a reference whiteboard, and repeating the foregoing operations;
   performing uniformity correction on the diffuse reflection image, demodulating the image, and extracting an alternating current component; and
   inputting the alternating current component image to a trained disease detection model, and determining whether the crop sample has a disease.

8. The detection method according to claim 7, wherein each spatial frequency adopts three phases: 0, $2\pi/3$, and $4\pi/3$.

9. The detection method according to claim 8, wherein a specific process of the image modulation comprises:
   demodulating the diffuse reflection image by using a formula $$M_{AC}(x, f_x) = \frac{\sqrt{2}}{3}\left[(I_1 - I_2)^2 + (I_2 - I_3)^2 + (I_3 - I_1)^2\right],$$

to obtain a diffuse reflection amplitude envelope curve of the crop sample to be detected; and
   then calculating the alternating current component of the image by using the formula $I_{AC}(x,f_x)=M_{AC}(x,f_x)\cdot\cos(2\pi f_x+\alpha)$;
   wherein $I_1$, $I_2$, and $I_3$ respectively reflection intensities of pixels of the diffuse reflection image of the crop sample to be detected in the three phases, $f_x$ is a spatial frequency of a light source, and a is a spatial phase of the light source.

10. The detection method according to claim 9, wherein the trained disease detection model is obtained by the following steps:

extracting features of the alternating current component of the diffuse reflection image, clustering the extracted features, constructing a Bag of words, classifying all the features of the alternating current component image into different categories, then collecting statistics on a frequency of each category of the features, using the Bag of words of each picture as a feature vector, using a category of the picture as a label, and performing training to obtain the disease detection model.

11. A detection method using the portable apparatus for detecting early crop diseases according to claim 2, comprising the following steps:
   rotating the opening-and-closing skeleton, opening the light-shielding cloth, and putting a crop sample to be detected into the dark box body from a bottom;
   adjusting a shooting distance of the crop sample to a suitable distance through an observation port;
   closing the opening-and-closing apparatus, selecting a suitable projection optical wavelength, controlling the spatial frequency domain imaging apparatus to project structured light of sine grey scale patterns with different spatial frequencies to the crop sample to be detected; after the sine gray scale pattern is switched each time, acquiring, by the camera, a diffuse reflection image of a surface of the crop sample once; and opening all the opening-and-closing apparatuses, replacing the crop sample with a reference whiteboard, and repeating the foregoing operations;
   performing uniformity correction on the diffuse reflection image, demodulating the image, and extracting an alternating current component; and
   inputting the alternating current component image to a trained disease detection model, and determining whether the crop sample has a disease.

12. The detection method according to claim 11, wherein each spatial frequency adopts three phases: 0, $2\pi/3$, and $4\pi/3$.

13. The detection method according to claim 12, wherein a specific process of the image modulation comprises:
   demodulating the diffuse reflection image by using a formula $$M_{AC}(x, f_x) = \frac{\sqrt{2}}{3}[(I_1 - I_2)^2 + (I_2 - I_3)^2 + (I_3 - I_1)^2],$$

to obtain a diffuse reflection amplitude envelope curve of the crop sample to be detected; and
   then calculating the alternating current component of the image by using the formula $I_{AC}(x,f_x)=M_{AC}(x,f_x)\cdot\cos(2\pi f_x+\alpha)$;
   wherein $I_1$, $I_2$, and $I_3$ respectively reflection intensities of pixels of the diffuse reflection image of the crop sample to be detected in the three phases, $f_x$ is a spatial frequency of a light source, and a is a spatial phase of the light source.

14. The detection method according to claim 10, wherein the trained disease detection model is obtained by the following steps:
   extracting features of the alternating current component of the diffuse reflection image, clustering the extracted features, constructing a Bag of words, classifying all the features of the alternating current component image into different categories, then collecting statistics on a frequency of each category of the features, using the Bag of words of each picture as a feature vector, using a category of the picture as a label, and performing training to obtain the disease detection model.

15. A detection method using the portable apparatus for detecting early crop diseases according to claim 3, comprising the following steps:
   rotating the opening-and-closing skeleton, opening the light-shielding cloth, and putting a crop sample to be detected into the dark box body from a bottom;
   adjusting a shooting distance of the crop sample to a suitable distance through an observation port;
   closing the opening-and-closing apparatus, selecting a suitable projection optical wavelength, controlling the spatial frequency domain imaging apparatus to project structured light of sine grey scale patterns with different spatial frequencies to the crop sample to be detected; after the sine gray scale pattern is switched each time, acquiring, by the camera, a diffuse reflection image of a surface of the crop sample once; and opening all the opening-and-closing apparatuses, replacing the crop sample with a reference whiteboard, and repeating the foregoing operations;
   performing uniformity correction on the diffuse reflection image, demodulating the image, and extracting an alternating current component; and
   inputting the alternating current component image to a trained disease detection model, and determining whether the crop sample has a disease.

16. The detection method according to claim 15, wherein each spatial frequency adopts three phases: 0, $2\pi/3$, and $4\pi/3$.

17. The detection method according to claim 16, wherein a specific process of the image modulation comprises:
   demodulating the diffuse reflection image by using a formula $$M_{AC}(x, f_x) = \frac{\sqrt{2}}{3}[(I_1 - I_2)^2 + (I_2 - I_3)^2 + (I_3 - I_1)^2],$$

to obtain a diffuse reflection amplitude envelope curve of the crop sample to be detected; and
   then calculating the alternating current component of the image by using the formula $I_{AC}(x,f_x)=M_{AC}(x,f_x)\cdot\cos(2\pi f_x+\alpha)$;
   wherein $I_1$, $I_2$, and $I_3$ respectively reflection intensities of pixels of the diffuse reflection image of the crop sample to be detected in the three phases, $f_x$ is a spatial frequency of a light source, and a is a spatial phase of the light source.

18. The detection method according to claim 6, wherein the trained disease detection model is obtained by the following steps:
   extracting features of the alternating current component of the diffuse reflection image, clustering the extracted features, constructing a Bag of words, classifying all the features of the alternating current component image into different categories, then collecting statistics on a frequency of each category of the features, using the Bag of words of each picture as a feature vector, using a category of the picture as a label, and performing training to obtain the disease detection model.

19. A detection method using the portable apparatus for detecting early crop diseases according to claim 4, comprising the following steps:

rotating the opening-and-closing skeleton, opening the light-shielding cloth, and putting a crop sample to be detected into the dark box body from a bottom;

adjusting a shooting distance of the crop sample to a suitable distance through an observation port;

closing the opening-and-closing apparatus, selecting a suitable projection optical wavelength, controlling the spatial frequency domain imaging apparatus to project structured light of sine grey scale patterns with different spatial frequencies to the crop sample to be detected; after the sine gray scale pattern is switched each time, acquiring, by the camera, a diffuse reflection image of a surface of the crop sample once; and opening all the opening-and-closing apparatuses, replacing the crop sample with a reference whiteboard, and repeating the foregoing operations;

performing uniformity correction on the diffuse reflection image, demodulating the image, and extracting an alternating current component; and inputting the alternating current component image to a trained disease detection model, and determining whether the crop sample has a disease.

20. The detection method according to claim 19, wherein each spatial frequency adopts three phases: 0, $2\pi/3$, and $4\pi/3$.

* * * * *